(12) United States Patent
Zabaneh et al.

(10) Patent No.: US 11,147,893 B1
(45) Date of Patent: Oct. 19, 2021

(54) PATHOGEN-RICH SURFACE SANITIZING SYSTEM AND METHOD

(71) Applicants: Mike Zabaneh, San Francisco, CA (US); Ronald Perkes, Novato, CA (US)

(72) Inventors: Mike Zabaneh, San Francisco, CA (US); Ronald Perkes, Novato, CA (US)

(73) Assignee: Tangent Computer Inc., Burlingame, CA (US)

( * ) Notice: Subject to any disclaimer, the term of this patent is extended or adjusted under 35 U.S.C. 154(b) by 1 day.

(21) Appl. No.: 17/012,132

(22) Filed: Sep. 4, 2020

(51) Int. Cl.
*A61L 2/10* (2006.01)
*A61L 2/26* (2006.01)
*A61L 2/24* (2006.01)

(52) U.S. Cl.
CPC ........ *A61L 2/10* (2013.01); *A61L 2/24* (2013.01); *A61L 2/26* (2013.01); *A61L 2202/10* (2013.01)

(58) Field of Classification Search
USPC .......................................................... 422/24
See application file for complete search history.

(56) References Cited

U.S. PATENT DOCUMENTS

| | | | | |
|---|---|---|---|---|
| 3,872,349 A * | 3/1975 | Spero | ................... | H01J 65/044 315/39 |
| 6,242,753 B1 * | 6/2001 | Sakurai | ................... | A61L 2/08 250/504 R |
| 6,720,566 B2 * | 4/2004 | Blandford | ................ | F26B 3/28 250/504 R |
| 8,598,539 B2 * | 12/2013 | Chuang | .................. | B66B 1/466 250/455.11 |
| 9,370,600 B1 * | 6/2016 | DuPuis | ..................... | A61L 9/20 |
| 2011/0291995 A1 * | 12/2011 | Shr | .......................... | A61L 2/10 345/176 |

\* cited by examiner

*Primary Examiner* — Phillip A Johnston
(74) *Attorney, Agent, or Firm* — Taylor Intellectual PLLC; James W. Taylor, II

(57) ABSTRACT

Surfaces are sanitized by using radiation (such as UV-C) to kill pathogens (such as bacteria). A lamp shade is provided that shapes the radiation from a sanitizing lamp into an intended projection pattern, which is irradiated on a target area to kill pathogens in that target area. The radiation is controlled and turned on autonomously based upon sensors that determine when no one is using the device being sanitized.

20 Claims, 4 Drawing Sheets

PATHOGEN-RICH SURFACE SANITIZING SYSTEM AND METHOD

FIELD OF THE INVENTION

The present invention relates to sanitization of surfaces from pathogens by using radiation. In particular, the present invention relates to sanitizing computer equipment in hospitals (such as a keyboard in an emergency room) by using sanitizing light (e.g., UV-C) from an integrated lamp.

BACKGROUND OF THE INVENTION

Pathogen infection—generally bacterial—is a common problem stemming from exposure to residual pathogens on surfaces in inter alia hospital environments. Pathogen infection poses serious medical issues, often more severe than the condition that brought a given patient to the hospital. Pathogens have the potential to cause serious illness, complicate simple surgeries or procedures, and even cause death.

Consider that in a hospital environment, surfaces are under consistent exposure from pathogens from ill patients, and often those pathogens can survive in atmospheric conditions for extended periods of time. Further, those pathogens may survive on a surface for an extended period as well. Exposure can be direct, such as a sick patient coughing on a surface, or can be indirect, such as a sick patient exposing another individual who then contacts another surface, transferring the pathogen. Once the surface has been exposed to the pathogen, any subsequent person or article could transfer the pathogen to a different patient or get infected with the pathogen itself, which significantly increases risks associated with treatment in busy hospitals. Once exposed, the pathogen can get into a patient's blood stream when the patient, e.g., touches his eyes or mouth.

Further, some pathogens, notably fungi or bacteria, can often reproduce in situ. While it is true that conditions can be fatal, many pathogens are quite robust and thrive in general conditions of a hospital, which promotes multiplying. Ultimately a transfer of a small amount of pathogen can lead to a large amount of pathogen being ultimately created, which can then be transferred all over a hospital. To prevent this situation, it is desirable to sterilize any surfaces that are commonly touched.

Therefore, a system and method are needed to sterilize a surface against pathogens.

BRIEF SUMMARY OF THE INVENTION

The present invention broadly provides an apparatus that has a target self-sterilizing region, wherein a mechanically secured or integrated sterilizing lamp assembly projects germicidal radiation onto a target sterilization area. Similar methods are provided.

In a first aspect of the invention, a self-sterilizing system is provided, comprising: a major surface of the system with a region to be sterilized; and a sterilizing lamp, secured to the system and adapted to emit germicidal radiation; wherein the sterilizing lamp shapes the germicidal radiation into a projected radiation pattern; and wherein the projected pattern substantially covers the self-sterilizing region. The sterilizing lamp may comprise a radiation source and a lamp shade. The lamp shade may not rotate, bend, or move relative to the system. The sterilizing lamp may be an ultraviolet C lamp. The aspect may comprise an activator. The activator may use data from a motion sensor or a timer to determine when to turn on the sterilizing lamp. The activator may automatically turn on the sterilizing lamp when an event is triggered based upon data from the motion sensor or timer. Data may be collected from a motion sensor, and the trigger to turn on the lamp may be passing of a predetermined period after the motion sensor quits detecting motion. Data may be collected from a timer, and the trigger to turn on the lamp can be a simple predetermined schedule.

In a second aspect of the invention, a method of sterilizing a self-sterilizing region on a housing is provided, comprising: providing a system to be sterilized; wherein the system comprises a housing with a surface exhibiting the self-sterilizing region; wherein the housing comprises a mechanically secured or integrated lamp assembly; wherein the lamp assembly comprises a sterilizing lamp adapted to emit germicidal radiation and a lamp shade; wherein the lamp shade shapes the germicidal radiation into a projected pattern; wherein the projected pattern substantially covers the self-sterilizing region; turning the lamp on to irradiate the self-sterilizing region with germicidal radiation. In another aspect of the invention, neither the housing nor the lamp shade moves or bends relative to the other. The projected pattern may substantially cover the self-sterilizing region. The sterilizing lamp may be an ultraviolet C lamp. The system may additionally comprise an activator. The lamp may automatically turn on by the activator. The activator may use data from a motion sensor or a timer to decide to turn on the sterilizing lamp. The data may be from a motion sensor. The data may be from a timer.

In a third aspect of the invention, a method of manufacturing a self-sterilizing system is provided, comprising: providing a major surface of the system with a region to be sterilized; providing a sterilizing lamp, adapted to emit germicidal radiation; securing the sterilizing lamp to the system such that: the sterilizing lamp shapes the germicidal radiation into a projected radiation pattern, and the projected pattern substantially covers the self-sterilizing region. The sterilizing lamp may comprise a radiation source and a lamp shade. The sterilizing lamp may be an ultraviolet C lamp.

BRIEF DESCRIPTION OF THE DRAWINGS

The following drawings illustrate by way of example and are included to provide further understanding of the invention for purpose of illustrative discussion of the embodiments of the invention. No attempt is made to show structural details of the embodiments in more detail than is necessary for a fundamental understanding of the invention, the description taken with the drawings making apparent to those skilled in the art how the several forms of the invention may be embodied in practice. Identical reference numerals do not necessarily indicate an identical structure. Rather, the same reference numeral may be used to indicate a similar feature or a feature with similar functionality. In the drawings.

DETAILED DESCRIPTION OF THE INVENTION

Figure 1:
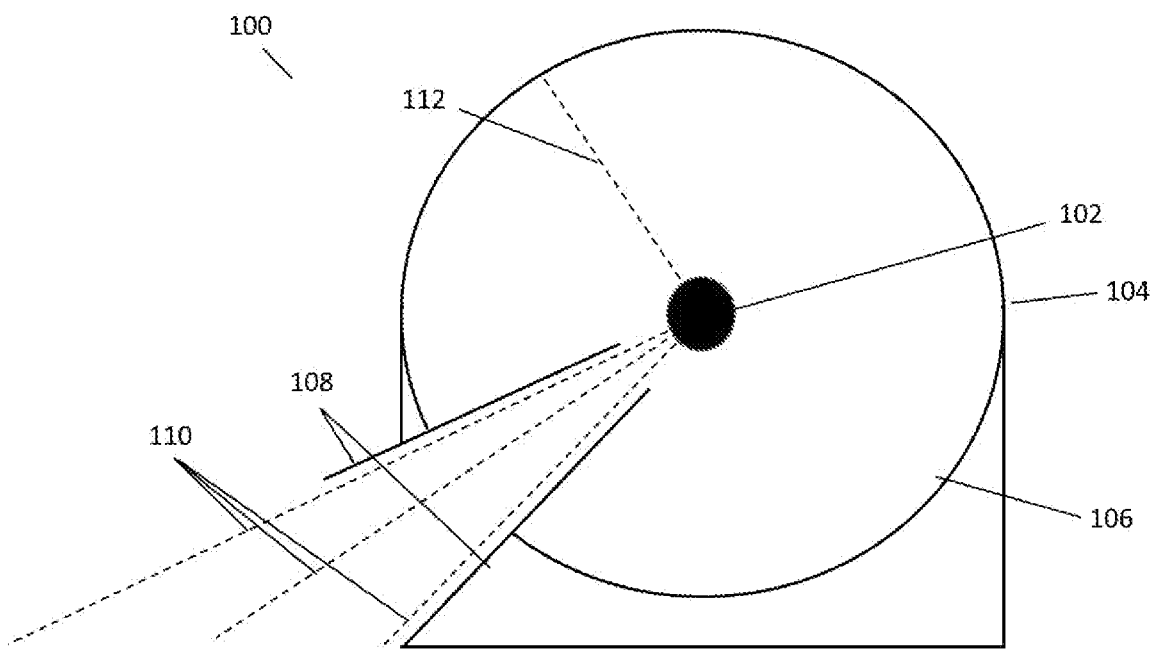
FIG. 1 illustrates a representation of a lamp assembly accord to an aspect of the present invention.

In a broad aspect of the invention, a sanitizing lamp is provided that is integrated with a system housing intended to be sanitized. By integrating the sanitizing lamp with the housing, coarse alignment is set in during manufacturing such that the sanitizing lamp will automatically project an intended course illumination pattern on the appropriate areas needing sanitization. While fine calibration could always be done, it is not necessary absent malfunction or damage to the system. In general, once the system leaves the factory, it will not need to be realigned or recalibrated unless the lamp, or if present a housing for the lamp, is removed from the system housing.

Sanitizing Lamp

A sanitizing lamp according to the present invention may emit radiation that disrupts normal pathogen activity in some way, generally by killing the pathogen. For example, the sanitizing lamp accord to the present invention may be an ultraviolet ("UV") based lamp, although any lamp that fulfills the objects and needs below are acceptable.

Ultraviolet C ("UV-C") may have germicidal properties. As such, the sanitizing lamp may be a UV-C lamp. UV-C emitted by the sun is nearly completely absorbed by the ozone and atmospheric layers, so there is only trace amount of UV-C detectable at the surface level of the earth's surface. Artificial lamps are one of the few, practical means to create UV-C on earth in any significant quantities. UV-C goes from about 100-280 nm in photon wavelength (about 3.10-4.13 eV particle energy in the photon).

The technology to produce any radiation is not particularly limited. Mercury vapor lamps, both high- and low-pressure varieties, can be used to produce UV-C. Low pressure mercury vapor lamps are preferred because they emit most of their radiant energy at 253.7 nm, which is in the UV-C spectrum and is a germicidal wavelength. Mercury vapor lamps could be hot cathode, cold cathode, slimline, high output, LEDs, or amalgam in various lengths, sizes, shapes, and pin configurations.

Amalgam UV lamps contain solid amalgam "spots". The actual amalgam spots are spots of mercury alloy (generally mercury with indium or gallium), which are used with known physical characteristics of mercury and the other metals in the alloy to control the vapor pressure of mercury via stead-state calculations. Overall, amalgam UV lamps have superior lifetimes compared to other mercury vapor lamps.

UV-C LEDs are in their infancy, but they can be used for germicidal applications. While UV-based LEDs are being researched, UV-C LEDs are believed to be the future of UV-C production. Therefore, they are within the scope of this specification.

A sanitizing lamp according to the present invention may be capable of killing a significant amount of pathogen—herein meaning at least 90% of the number of a given pathogen—in an exposure of six hours or less, four hours or less, two hours or less, one hour or less, 30 minutes or less, twenty minutes or less, ten minutes or less or five minutes or less. In a preferred embodiment, the sanitizing lamp can kill 95% of a pathogen in an exposure of six hours or less, four hours or less, two hours or less, one hour or less, 30 minutes or less, twenty minutes or less, ten minutes or less or five minutes or less. More preferably the sanitizing lamp can kill 99% of a pathogen in an exposure of six hours or less, four hours or less, two hours or less, one hour or less, 30 minutes or less, twenty minutes or less, ten minutes or less or five minutes or less. Yet even more preferably the sanitizing lamp can kill 99.9% of a pathogen in six hours or less, four hours or less, two hours or less, one hour or less, 30 minutes or less, twenty minutes or less, ten minutes or less or five minutes or less.

Alternatively, the sanitizing lamp can otherwise disrupt normal pathogen activity. In this event, the levels of disruption are comparable to the numbers and timeline above for killing the pathogen. Exemplary methods of disrupting the pathogen are: denaturing the pathogen; preventing the pathogen from reproducing; flocculating the pathogen such that it aggregates and fails to function as a pathogen; injuring the pathogen such that it no longer functions as a pathogen; etc. Critically, the present invention requires that the pathogen is disrupted such that it no longer functions properly as a pathogen.

Lamp Shade

While not strictly required, a lamp shade is highly beneficial to shape the projection pattern of the sanitizing lamp. Given that the present invention is configured to be secured to the object to be sanitized, the shade may be beneficial to control the radiation projection pattern. If no shade is present, then radiation can escape in generally any direction. The effects of this could weaken radiation in the target area, and stray radiation that could have unintended effects, such as aging plastics, rubbers, and the like, or could expose an animal—such as a human patient—to the UV-C, which could result in a sunburn or worse. Generally, a lamp shade will always be present except for when the sanitizing lamp is intended to sanitize in all directions, such as when the lamp shade is inside of a sanitizing chamber or the like.

The lamp shade can be of a material and thick enough such that radiation does not bleed through the lamp shade in any significant quantities. The lamp shade may remove at least 90% of sanitizing radiation in directions other than the intended protection pattern. More preferably the lamp shade can remove at least 95% of sanitizing radiation in directions other than the intended protection pattern. Even more preferably the lamp shade can remove at least 99% of sanitizing radiation in directions other than the intended protection pattern. Yet even more preferably the lamp shade can remove at least 99.9% of sanitizing radiation in directions other than the intended protection pattern. The lamp shade can be made of a material that holds shape well, or can be trimmed or supported by a material that holds shape well, such that the projected radiation pattern does not change with time. Exemplary materials for the lamp shade are: metals, such as iron, nickel, copper, tin, aluminum, zinc, chromium, titanium, cobalt, molybdenum, palladium, zirconium, rhodium, noble metals (e.g., gold, platinum, silver), beryllium, ruthenium, and alloys thereof; plastics, such as polystyrene, poly(vinyl chloride), polyethylene (including amorphous, low density, and high density varieties), polypropylene, polyesters (including poly(ethylene terephthalate)), acrylonitrile-butadiene-styrene, polycarbonate, polyacrylates (including poly(methyl acrylate)), polymethacrylates (including poly(methyl methacrylate)), poly(acrylic acid), substituted versions of any of the foregoing, copolymers thereof (including random, block, syndiotactic, and dendritic), cross-linked versions thereof, and other chemically similar compounds; hard elastomers, such as polyisoprene, styrene-butadiene rubber, polybutadiene rubber, acrylonitrile rubber, isobultylene-isoprene copolymer, ethylene-propylene rubber, polychloroprene, polysulfide, poly(dimethyl siloxane), chlorinated polyethylene, polyacrylate elastomers, ethylene-propylene-butadiene rubbers, fluoroelastomers (including as FKM, FFKM, and polytetrafluoroethylene), substituted versions of any of the foregoing, copolymers thereof (including random, block, syndiotactic, and dendritic), cross-linked versions thereof, and other chemically similar compounds; and opaque ceramics, such as alumina, barium titanate, boron oxide, boron nitride, earthenware, ferrite, porcelain, sailon, silicon carbide, silicon nitride, steatite, and zinc oxide.

The inside of the lamp shade may be reflective such that radiation projected into the lamp shade is not lost, but is reflected back to the source, which increases the irradiative efficiency of a lamp assembly—in this context, a lamp assembly means a lamp shade and a sanitizing lamp. As would be appreciated by one of ordinary skill in the art, if the inside of the lamp shade is reflective, the shape of the inside of the shape is particularly important. Radiation reflecting inside the shade may change the angle that the light leaves the assembly. Without properly shaping the reflective surfaces, radiation may bounce to unexpected angles losing efficiency on the target area and increasing the chance of unintended exposure to bystanders, such as a sick patient or child in the emergency room. Therefore, shaping the inside of the shade may be of critical importance.

For example, consider the present FIG. 1. Lamp assembly 100 is shown. Sanitizing lamp 102 is present in the middle of the assembly 100. The lamp shade 104 of the lamp assembly 100 is opaque and does not let sanitizing radiation out of the assembly 100 or other radiation into the assembly 100. Reflective inner surface 106 of the assembly 100 allows radiation to reflect inside the assembly 100. As the result, radiation efficiency is maximized. Radiation guides 108 shape protected radiation 110 into an intended projection pattern. The reflective surface 106 of this exemplary lamp assembly 100 is circular. Therefore, errand radiation 112 will be reflected roughly back to the lamp 102. Due to imperfections in the reflective surface 106, the light will bend and either be reabsorbed by some surface inside the shade, or will be emitting between guides 108 in a roughly controlled intended projection pattern.

Figure 2:
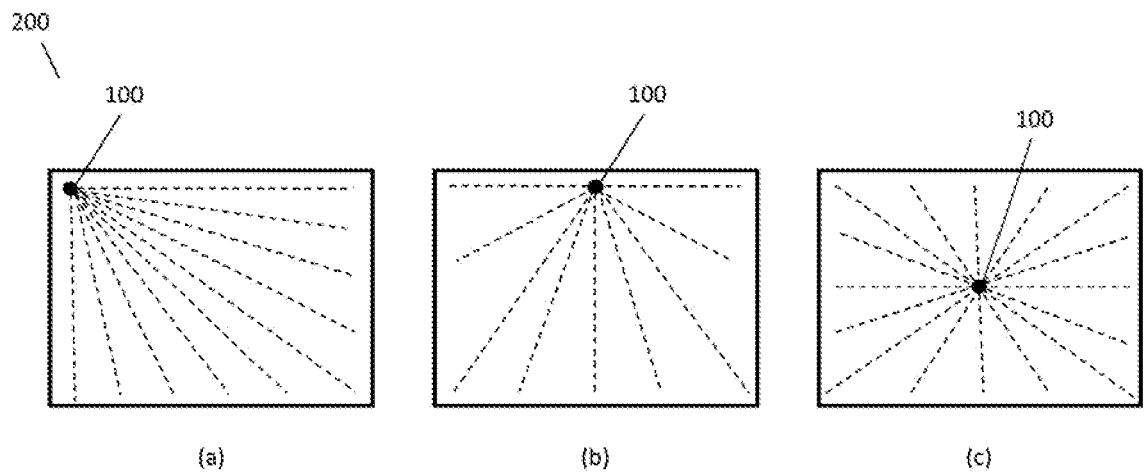
FIG. 2 illustrates projected illumination patterns emitting from the lamp assembly according to an aspect of the present invention.

Note that while FIG. 1 only has one exit on one side of the lamp assembly, generally, the lamp assembly 100 will be adapted to allow an intended projection pattern in 360°, 180°, or 90°, as the assembly 100 will be sitting at the edge (180°), corner (90°), or middle (360°), of the intended projection pattern. See, for example, FIG. 2, wherein the dashed lines represent the intended projection pattern. In FIG. 2(a), the lamp assembly 100 is sitting in the corner of the target area projecting in 90°. In FIG. 2(b), the lamp assembly 100 is sitting at the edge of the target area projecting in 180°. In FIG. 2(c), the lamp assembly 100 is sitting in the middle of the target area projecting in 360°. While in FIG. 3(c), the lamp assembly 100 is literally in the "center" of the target area, it can be off center as well. Other angles, such as inter alia 60°, 30°, 270° are within the scope of the present invention but are known shows as they are within the skill of the art in view of the present disclosure.

Figure 3:
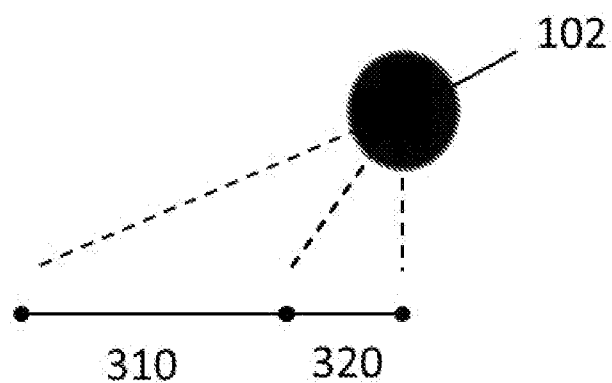
FIG. 3 illustrates a schematic of a lamp assembly illuminating on near and far surfaces accord to an aspect of the present invention.

As would be appreciated by the skilled artisan, the lamp assembly in general will be raised above the target surface it will be radiating. If it is not raised above the target surface, it cannot irradiate that surface for geometric and physical reasons. However, the amount it is raised off of the surface can be minimized. There are two considerations. First, the closer to the target surface the lamp is, the more dense the radiation will be compared to the same radiation source at a further distance. Second, as is shown in FIG. 3, the target area nearest the lamp 102 will generally get more radiation than target area further than the lamp 102. Consider that if photons are sent out by lamp 102 homogeneously, because flat surface 310 is larger than flat surface 320 owing to the angle of photons relative to the surface, the photons spread out evenly to cover the area more on surface 310 and will be more sparse.

The lamp shade and lamp assembly may be rigid and attached directly to or integrated with the system housing. Optionally, the system housing and the lamp assembly does not move or bend relative to each other, as that creates the potential for misalignment or miscalibration. In one embodiment, by permanently attaching the lamp shade and lamp assembly to the system housing, upon a proper assembly, the lamp assembly will inherently irradiate the proper target area unless the system malfunctions, the system is damaged, or the system is disassembled.

Alternatively, in the case of a laptop for example, the system housing and the lamp assembly can bend relative to each other. Or the lamp assembly can be spring loaded such that when the laptop is closed it is spring biased into a recess in the laptop housing and becomes flush. But when the laptop is opened, the spring pushes the lamp assembly out of the laptop housing so that it can irradiate the laptop. In this event, the lamp shade needs to be mechanized and capable of moving relative to the system housing, so that it can synchronize its movements with the bend of the system housing (e.g., when a laptop opens or closes, the shade moves and changes its shape such that the target area is substantially covered by the projected radiation pattern but still minimizes stay radiation).

Further the skilled artisan would recognize that art techniques could be adapted herein to modify the lamp shade or lamp assembly. For example, the lamp shade shown in FIG. 1 could be automated or the entire assembly of FIG. 1 could be automated to only self-sanitize a small portion of the target self-sanitizing area at a time, but the radiation pattern could be moved according to a pattern, randomly, or through intelligent code.

For example, the lamp assembly could move in a raster pattern, a modified raster pattern, or randomly around the target surface, sanitizing one area at a time.

System

The system of the present invention is not particularly limited. The system can be any device that has a target area, generally on a housing for the system. The target area need only be one in which one wishes to kill pathogens thereon. In a hospital environment, keyboards, monitors, and the like may all be systems according to the invention. Moreover, an entire computer, such as a laptop, may be the system.

Laptops have moving parts. In particular, there is a hinge between the monitor and the keyboard. It is critical that the lamp, lamp shade, and target area do not move relative to each other. If they do (for example, the lamp is on a semi-rigid but bendable boom extension), then calibration and alignment is necessary. Or if the target area is on the keyboard area of a laptop, but the lamp and lamp shade are on the monitor portion of the laptop, then the two components move relative to each other because of the hinge between the monitor and keyboard portions of the laptop. This design is not within the scope of the present invention without modification because the projected pattern will move relative to the target area, so the device will only be effective if the laptop is in a correct position, which would require calibration and or alignment.

Alternatively, a system that had moving pieces (specifically a lamp and lamp shade that moved relative to the target area) would be within the scope of this disclosure if the lamp and/or lamp shade could move and stay synchronized to the target area. This could be accomplished by have a way to measure the movement and take appropriate correction. For example, in the case of a laptop, a calibration could be performed during manufacturing on a gauge that measured how far open the laptop was in degrees. Using the calibration data, the shade can move via a servo or the like that controls where the projected pattern is illuminated, such that the projected pattern follows the target area.

Further, the system could be any automated machine, such as an automated teller machine; a machine to check into to a flight, bus, or such; a lottery, slot machine, or other gambling device; a machine to order tickets at a theatre, a playhouse, an airport, a bus stop, or for any other purpose; or a point of sale machine at a retail store. Any machine that could be contaminated by pathogens-whether designed for a consumer, a retailer, a manufacturer, a hospital, or to be used in industry-could benefit from the present technology.

System Housing

By housing, the present inventors mean the outer boundary of the system, except hardware to secure the housing closed and to secure other objects, such as keyboards, mice, power cables, and similar accessories to the housing.

Beyond that, the system housing is not particularly limited. The system housing can be any housing for the system. The system housing can be made of a material that holds shape well, or can be trimmed or supported by a material that holds shape well, such that the target area does not move with time. Exemplary materials for the lamp shade are: metals, such as iron, nickel, copper, tin, aluminum, zinc, chromium, titanium, cobalt, molybdenum, palladium, zirconium, rhodium, noble metals (e.g., gold, platinum, silver), beryllium, ruthenium, and alloys thereof, plastics, such as polystyrene, poly(vinyl chloride), polyethylene (including amorphous, low density, and high density varieties), polypropylene, polyesters (including poly(ethylene terephthalate)), acrylonitrile-butadiene-styrene, polycarbonate, polyacrylates (including poly(methyl acrylate)), polymethacrylates (including poly(methyl methacrylate)), poly(acrylic acid), substituted versions of any of the foregoing, copolymers thereof (including random, block, syndiotactic, and dendritic), cross-linked versions thereof, and other chemically similar compounds; hard elastomers, such as polyisoprene, styrene-butadiene rubber, polybutadiene rubber, acrylonitrile rubber, isobultylene-isoprene copolymer, ethylene-propylene rubber, polychloroprene, polysulfide, poly(dimethyl siloxane), chlorinated polyethylene, polyacrylate elastomers, ethylene-propylene-butadiene rubbers, fluoroelastomers (including as FKM, FFKM, and polytetrafluoroethylene), substituted versions of any of the foregoing, copolymers thereof (including random, block, syndiotactic, and dendritic), cross-linked versions thereof, and other chemically similar compounds; and opaque ceramics, such as alumina, barium titanate, boron oxide, boron nitride, earthenware, ferrite, porcelain, sailon, silicon carbide, silicon nitride, steatite, and zinc oxide.

Automation

The present invention may be automated. It may comprise an activator to automate when precisely the lamp turns on. The activator can trigger automatically when certain events occur.

For example, the activator use data from a motion sensor. In this event, a turn on event for the lamp may be triggered after the motion sensor detects motion on the surface of the system housing but then no longer detects motion for a predetermined amount of time. The activator may activate the lamp at different voltages or lengths of time, depending on the output of the motion sensor. For example, the motion sensor may give strong readings, so the activator sends strong voltages to the lamp (assuming the lamp has a linear response to voltage). The activator may turn on the lamp for a period of time, according to a formula. For example, it may choose to turn on the lamp for twice as long as it detected motion plus five minutes. In some environments, where system utilization is high, it may be beneficial for the system to only turn on for short strong periods of time. The activator may be controllable (e.g., if the activator is a component of a computer or controlled by a computer), such that a user can precisely determine the triggers that would turn on the lamp and the details of how long the lamp is on, voltage, etc. Further, if a motion sensor gives input to or controls the activator, it may be beneficial that a trigger exists to turn off the lamp if the motion sensor detects any motion at or near the target irradiation area to prevent irradiating a person.

In another example, the activator may use data from a timer. In this event, it merely triggers itself at predetermined intervals or using a schedule. In the event both a timer and a motion sensor provide data to the activator, it may be beneficial that the motion sensor can turn off the lamp even if it was data from the timer that turned on the lamp, for the reasons above.

When the lamp is under automated control, it may also be beneficial that the lamp can be placed under manual control, overriding the automatic settings. Such is well within the ordinary skill of the art in view of the present disclosure.

Any art recognized automation method can be used to automate the present invention, beyond what has been disclosed herein.

Example 1

Figure 4:
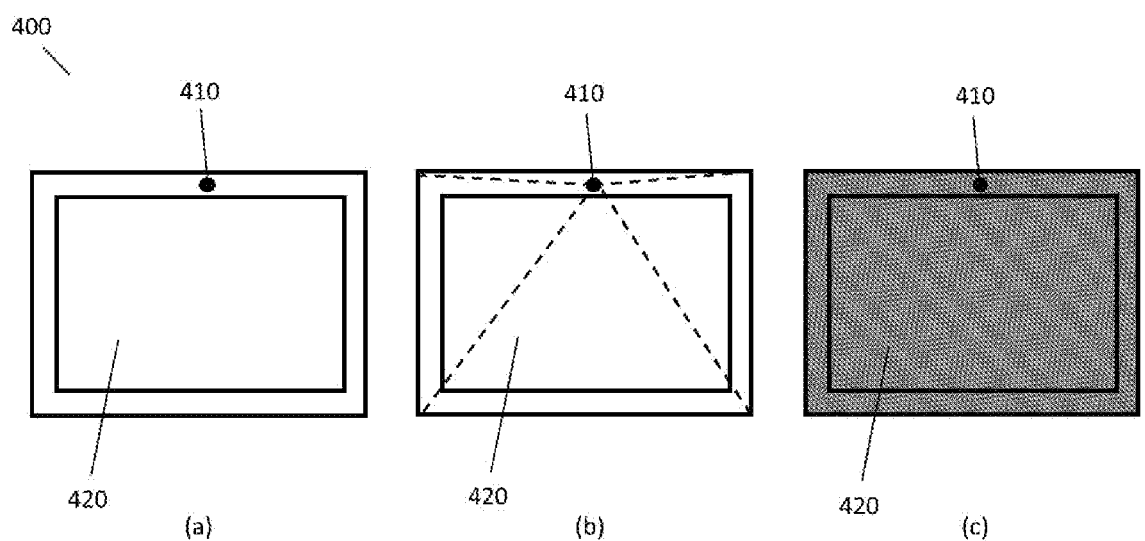
FIG. 4 illustrates a schematic of a first example of the present invention (e.g., a monitor).

Referring to FIG. 4, inventive touchpad monitor 400 has a lamp assembly 410 sitting within the target radiation area but offset from the center. In FIG. 4(a), only the raw components are shown. Lamp assembly 410 comprises a UV-C lamp (not shown) and a lamp shade (not shown). Lamp assembly 410 is designed to radiate at least all of the touchscreen portion 420 of monitor 400. FIG. 4(b) shows the "corners" of the actual projected pattern from the lamp assembly 410 in dashed lines. The target area is shown by the shaded background pattern in FIG. 4(c). By comparing FIGS. 4(b) and 4(c), one can observe that the intended target area is illuminated and substantially and fully covered. The skilled artisan would appreciate that the shape of the lamp shade assembly can be fine-tuned such to maximize intended coverage and minimize radiation spill outside of the target area.

Example 2

Figure 5:
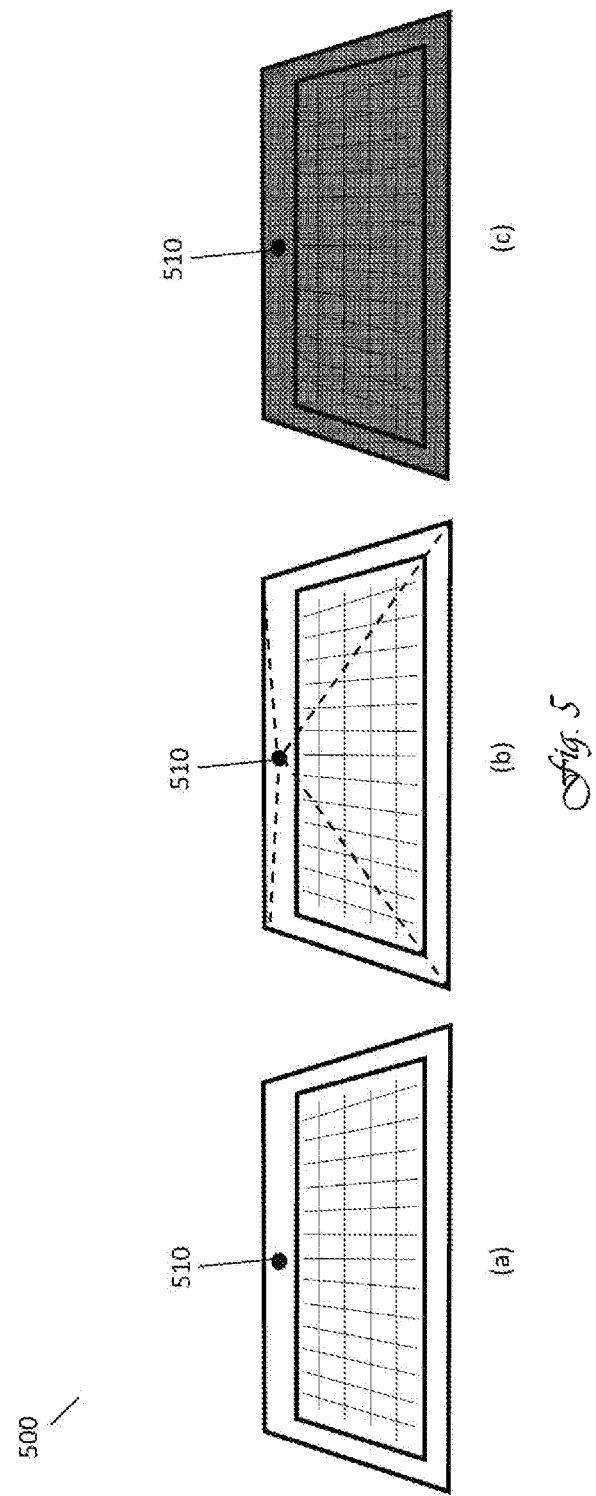
FIG. 5 illustrates a schematic of a second example of the present invention (e.g., a keyboard).

Referring to FIG. 5, inventive keyboard 500 has a lamp assembly 510 sitting within the target radiation area but offset from the center. In FIG. 5(a), only the raw components are shown. Lamp assembly 510 comprises a UV-C lamp (not shown) and a lamp shade (not shown). Lamp assembly 510 is positioned to radiate at the top portion of keyboard 500. FIG. 5(b) shows the "corners" of the actual projected pattern from the lamp assembly 510 in dashed lines. The target area is shown by the shaded background pattern in FIG. 5(c). By comparing FIGS. 5(b) and 5(c), one can observe that the intended target area is illuminated and substantially and fully covered. The skilled artisan would appreciate that the shape of the lamp shade assembly can be fine-tuned such to maximize intended coverage and minimize radiation spill outside of the target area.

Example 3

Figure 6:
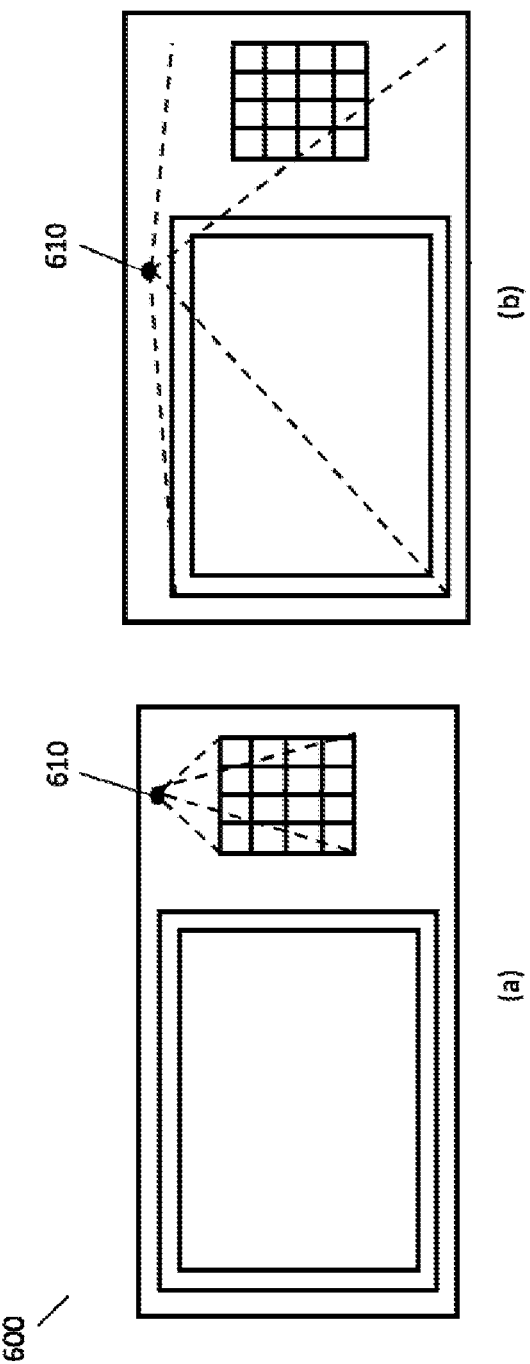
FIG. 6 illustrates a schematic of a third example of the present invention (e.g., an automated terminal).

Referring to FIG. 6, inventive automated station 600 has a screen 620 to display information to a user. The automated station 600 can be an automated teller machine; a machine to check into to a flight, bus, or such; a lottery, slot machine, or other gambling device; a machine to order tickets at a theatre, a playhouse, an airport, a bus stop, or for any other purpose; a point of sale machine at a retail store; or any other automated machine. Further, the automated station 600 has a lamp assembly 610. In FIG. 6(a), the lamp assembly 610 is placed directly over a commonly used keypad 630, placed to irradiate only the keypad, which is the most probable nucleus for spreading pathogens from this station 600. The keypad 630 would benefit from radiation from radiation, and therefore lamp assembly 610 has been added to periodically, automatically sanitize the keypad 630. In this subembodiment, it may be economically or otherwise undesirable to sanitize the monitor 620, and therefore in this embodiment it is not being sanitized, demonstrating that there is some level of engineering and business choice as to what parts of a device are sanitized. In FIG. 6(b), the lamp assembly 610 is position over both the monitor 620 and the keypad 630 to demonstrate that the lamp assembly 610 can sanitize the whole apparatus is desirable.

It will also be recognized by those skilled in the art that, while the invention has been described above in terms of preferred embodiments, it is not limited thereto. Various features and aspects of the above described invention may be used individually or jointly. Indeed, individual components described may not be present, may be different, may be present in a different number (as a plurality when described as singular, as singular when described as a plurality, or as a different sized plurality). Further, although the invention has been described in the context of its implementation in a particular environment, and for particular applications (e.g. computers used in hospitals), those skilled in the art will recognize that its usefulness is not limited thereto and that the present invention can be beneficially utilized in any number of environments and implementations where it is desirable to sanitize a surface. Accordingly, the claims set forth below should be construed in view of the full breadth and spirit of the invention as disclosed herein.

For the purposes of this specification, please consider the below definitions. Be advised that these definitions are not necessarily the only definitions in this specification. Some terms may be defined more precisely below, or my otherwise deviate from their art standard meaning.

"Secured to"—this term means that the subject and object of this phrase (A and B in the phrase "A is secured to B") are secured together by any technology such that they do not move relative to each other unless the system intends for them to move relative to each other. For example, they could be glued, bolted, screwed into place, jointed, welded, soldered, or joined in any temporary or permanent way that would prevent the subject and object of the phrase from substantially moving relative to each other. In more complicated examples, they could be connected via a servo, spring biased pop-out component, or similar.

"Major surface"—this means the surface of the housing or object that has the target area to be irradiated. The major surface "Substantially covers"—this term is used in the context of a target area on a surface and an actual projected pattern on the target area; the area is substantially covered if at least 90% of the target area is covered by the actual projected pattern.

"Significant," "substantial," "substantially all," and other forms of these words and phrases generally modify numbers to mean plus or minus five percent. They modify object arrangements and other physical characteristic to mean that the arrangement or characteristic is basically achieved, although there may be some error in the arrangement or characteristic, e.g., and arrangement that substantially seals may generally seal but not have a perfect seal. Failure to use one of these terms does not imply that the claimed or described condition requires perfection without error, but the use of these terms is to explicitly include those arrangements characteristics with small error.

The invention claimed is:

1. A target area sterilizing system, comprising:
   a major surface of the system with a region to be sterilized;
   a sterilizing lamp, secured to the system and adapted to emit germicidal radiation; and
   a lamp shade;
   wherein the sterilizing lamp shade is rigid and mechanically secured to or integrated with the system housing and efficiently shapes the germicidal radiation into a projected radiation pattern to irradiate and sterilize the irradiation target area efficiently.

2. The target area sterilizing system of claim 1, wherein when the lamp shade is adjustable.

3. The target area sterilizing system of claim 1, wherein the lamp shade does not rotate, bend, or move relative to the system and maximizes radiation guidance to the target area.

4. The target area sterilizing system of claim 1, wherein the sterilizing lamp is an ultraviolet C lamp.

5. The target area sterilizing system of claim 1, additionally comprising an activator.

6. The target area sterilizing system of claim 5, wherein the activator uses data from a motion sensor or a timer to determine when to turn on the sterilizing lamp, and wherein the activator automatically turns on the sterilizing lamp when an event is triggered based upon data from the motion sensor or timer.

7. The target area sterilizing system of claim 6, wherein the data is from a motion sensor, and the trigger to turn on the lamp is passing of a predetermined period of time after the motion sensor quits detecting motion.

8. The target area sterilizing system of claim 6, wherein the data is from a timer, and the trigger to turn on the lamp occurs on a predetermined schedule.

9. A method of sterilizing a target area sterilizing region on a housing comprising,
   providing a system to be sterilized;
      wherein the system comprises a housing with a surface exhibiting the target area sterilizing region;
      wherein the housing comprises a mechanically secured or integrated lamp assembly;
      wherein the lamp assembly comprises a sterilizing lamp adapted to emit germicidal radiation and a lamp shade;
      wherein the lamp shade efficiently shapes the germicidal radiation into a projected pattern;
      wherein the projected pattern substantially covers the target area sterilizing region; and
   turning the lamp on to irradiate the target area sterilizing region with germicidal radiation.

10. The method of sterilizing a target area sterilizing region of claim 9, wherein neither the housing nor the lamp shade move or bend relative to each other and wherein the projected pattern substantially covers the target area sterilizing region.

11. The method of sterilizing a target area sterilizing region of claim 9, wherein the lamp shade is adjustable.

12. The method of sterilizing a target area sterilizing region of claim 9, wherein the sterilizing lamp is an ultraviolet C lamp.

13. The method of sterilizing a target area sterilizing region of claim 9, wherein the system additionally comprises an activator.

14. The method of sterilizing a target area sterilizing region of claim 13, wherein the lamp was automatically turned on by the activator.

15. The method of sterilizing a target area sterilizing region of claim 14, wherein the activator used data from a motion sensor or a timer to programmatically turn on the sterilizing lamp.

16. The target area sterilizing system of claim 15, wherein the data was from a motion sensor.

17. The target area sterilizing system of claim 9, wherein the irradiation target area is tuned based on the shade.

18. A method of manufacturing a target area sterilizing system, comprising:
   providing a major surface of the system with a region to be sterilized;
   providing a sterilizing lamp, adapted to emit germicidal radiation;
   providing a lamp shade, adapted to shape the germicidal radiation; and
   securing the sterilizing lamp shade to the system such that: the sterilizing lamp shade efficiently shapes the germicidal radiation into a projected radiation pattern, and the projected pattern substantially covers a target area sterilizing region.

19. The method of manufacturing a target area sterilizing system of claim 18, wherein the sterilizing lamp comprises a radiation source and lamp shade is adjustable.

20. The method of manufacturing a target area sterilizing system of claim 18, wherein the sterilizing lamp is an ultraviolet C lamp.

* * * * *